United States Patent
White

(10) Patent No.: US 9,956,150 B2
(45) Date of Patent: May 1, 2018

(54) DENTAL CUTTING LUBRICANT AND METHOD OF USE THEREOF

(71) Applicant: John Irving White, Asheville, NC (US)

(72) Inventor: John Irving White, Asheville, NC (US)

(*) Notice: Subject to any disclaimer, the term of this patent is extended or adjusted under 35 U.S.C. 154(b) by 0 days. days.

(21) Appl. No.: 15/673,941

(22) Filed: Aug. 10, 2017

(65) Prior Publication Data
US 2017/0333313 A1 Nov. 23, 2017

Related U.S. Application Data

(63) Continuation-in-part of application No. 15/457,427, filed on Mar. 13, 2017, now abandoned.

(60) Provisional application No. 62/306,674, filed on Mar. 11, 2016.

(51) Int. Cl.

| | | |
|---|---|---|
| *A61K 8/34* | (2006.01) | |
| *A61K 8/92* | (2006.01) | |
| *A61K 8/49* | (2006.01) | |
| *A61K 8/44* | (2006.01) | |
| *A61K 8/37* | (2006.01) | |
| *A61K 8/22* | (2006.01) | |
| *A61K 8/19* | (2006.01) | |
| *A61K 8/362* | (2006.01) | |
| *A61C 3/02* | (2006.01) | |
| *A61C 1/00* | (2006.01) | |
| *A61C 17/20* | (2006.01) | |
| *A61C 17/02* | (2006.01) | |
| *A61Q 11/00* | (2006.01) | |

(52) U.S. Cl.
CPC .............. *A61K 8/34* (2013.01); *A61C 1/0076* (2013.01); *A61C 1/0084* (2013.01); *A61C 3/02* (2013.01); *A61C 17/0202* (2013.01); *A61C 17/20* (2013.01); *A61K 8/19* (2013.01); *A61K 8/22* (2013.01); *A61K 8/345* (2013.01); *A61K 8/362* (2013.01); *A61K 8/37* (2013.01); *A61K 8/44* (2013.01); *A61K 8/4993* (2013.01); *A61K 8/922* (2013.01); *A61Q 11/00* (2013.01)

(58) Field of Classification Search
CPC ............ A61B 18/20; A61C 3/02; A61C 3/025
USPC ................. 433/26, 29, 80, 82, 104
See application file for complete search history.

(56) References Cited

U.S. PATENT DOCUMENTS

| | | | |
|---|---|---|---|
| 4,961,923 A | 10/1990 | Heyde | |
| 5,624,906 A | 4/1997 | Vermeer | |
| 5,785,521 A * | 7/1998 | Rizoiu | A61B 18/26 433/104 |
| 6,350,123 B1 * | 2/2002 | Rizoiu | A61B 18/201 433/29 |
| 6,676,409 B2 * | 1/2004 | Grant | A61C 3/025 433/88 |
| 7,320,594 B1 | 1/2008 | Rizolu et al. | |
| 7,601,731 B2 | 10/2009 | Raad | |
| 8,485,818 B2 * | 7/2013 | Boutoussov | A61C 1/0046 433/26 |
| 8,709,342 B2 | 4/2014 | Raad | |
| 9,078,441 B2 | 7/2015 | Raad | |
| 2006/0240381 A1 * | 10/2006 | Rizoiu | A61C 1/0046 433/80 |
| 2007/0098650 A1 | 5/2007 | Miller | |

* cited by examiner

*Primary Examiner* — Walter E Webb
(74) *Attorney, Agent, or Firm* — The Van Winkle Law Firm; William G. Heedy; David M. Carter

(57) ABSTRACT

The present invention provides a method for dental cutting including the steps of providing a dental unit water line irrigation system, the dental unit water line irrigation system including a container surrounding a solution chamber; providing a lubricant for use in the dental unit water line irrigation system, the lubricant defining a composition including 10 to 25% by weight of ethanol; 5 to 25% by weight of glycerol; 10 to 25% by weight of xylitol; 0.5 to 5% by weight of a nonionic surfactant and emulsifying agent; 0.15 to 0.5% by weight of a plurality of flavoring agents; and 45 to 60% by weight of water; and selectively operating the water line irrigation system to express the lubricant onto a dental cutting site.

12 Claims, 1 Drawing Sheet

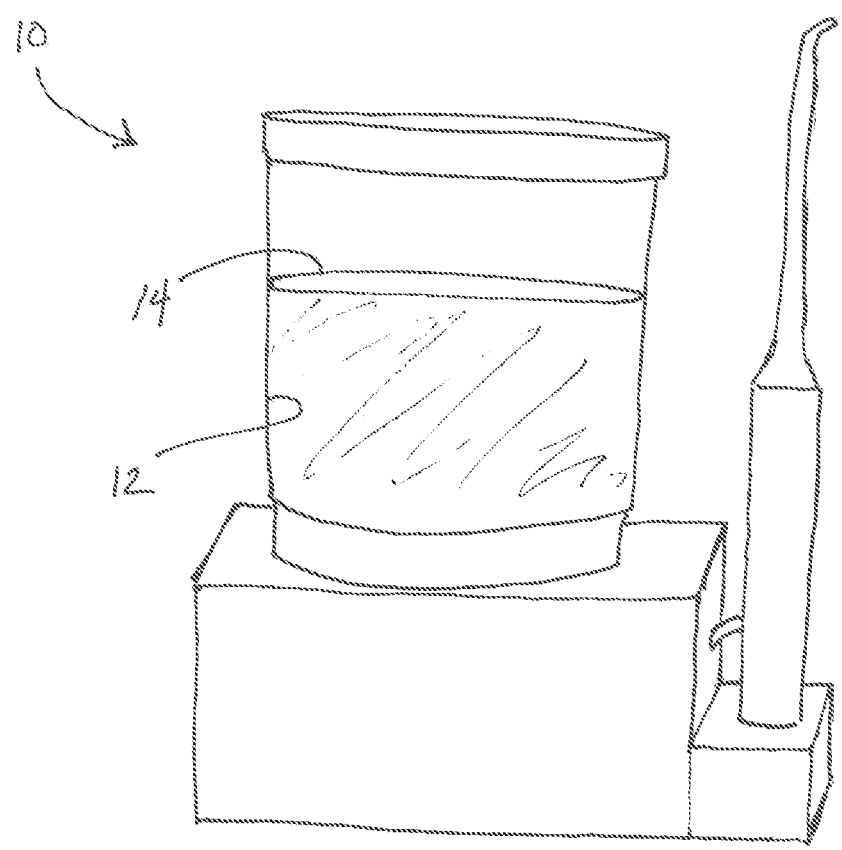

DENTAL CUTTING LUBRICANT AND METHOD OF USE THEREOF

RELATED APPLICATIONS

This patent application is a Continuation-In-Part Patent Application relating to and claiming the benefit of U.S. Non-Provisional patent application Ser. No. 15/457,427, which claims priority to and incorporates entirely by reference U.S. Provisional Patent Application Ser. No. 62/306,674 filed on Mar. 11, 2016.

FIELD OF THE INVENTION

This invention relates to a lubricant composition for increasing the efficiency and safety of cutting a tooth structure during dental procedures and a method of use thereof.

BACKGROUND OF THE INVENTION

For many years, dental burs have been used for cutting hard tissues—tooth or bone. They are generally made of steel, stainless steel, tungsten carbide and/or diamond grit. There are many bur shapes that are utilized in various specific procedures, such as cavity preparation and creating access points. Over the years, there have been a number of advancements, e.g. high-speed turbines, lasers and microabrasion, but a large majority of dentists still use the traditional hand piece and bur combination for the majority of their clinical work.

Dental cutting or polishing procedures must be performed under a coolant to avoid side effects caused by heating during operation of the cutting instrument. High Speed and Low Speed dental hand pieces have utilized water spray as a cutting fluid for many years. In designing early systems, municipal water system supply lines were simply connected directly to the dental unit. This water was then distributed throughout the dental unit via small diameter tubing water lines leading to the dental hand piece, typically mixed with pressurized air and delivered as a fine spray aimed at the cutting interface between the dental bur and tooth structure. Water irrigation delivered in this manner provided benefit as it continually kept the site cleaner than dry preparation would by physically washing debris from the cutting site. A second benefit of irrigation is that it decreases the negative side effect of heat produced during cutting with fast rotational speeds of dental burs. Unchecked, such negative thermal effects can result in severe and possibly irreversible damage to the dental pulp, and are to be avoided. Therefore, keeping temperatures cool at the cutting interface of the dental bur and tooth structure is desirable.

Infection control in dentistry has increasingly become a concern, and in recent years there has been much concern over the growth of biofilm in small diameter water lines used to deliver water to the cutting site. Small amounts of bacteria are naturally present in municipal water systems. The presence of these bacteria, along with bacterial contamination potentially reintroduced back into the dental unit by retrograde fluid flow can potentially lead to bacterial colonization and biofilm formation in water lines. It has been demonstrated that there is a slower flowing outer column of water present inside small diameter water lines. This slower flowing column near the wall of small diameter lines means that bacterial contamination can remain for longer periods of time and results in proliferation of bacteria, and formation of biofilm that allows colonies of bacteria to firmly attach to the walls of water lines. This unchecked proliferation of the biofilm and colonies then leads to budding off of bacterial colonies by detachment. Once detached, the colonies then migrate downstream and could potentially result in contamination of the water delivered to the cutting site and, ultimately, exposure to the dental patient.

In an effort to address this contamination, dental unit manufacturers developed self-contained dental unit water line irrigation systems (S-CDUWLIS). This type of system, rather than being directly connected to the municipal water supply, utilizes a small bottle to contain water used for irrigation. The bottle is pressurized with compressed air above the water surface. Water is then siphoned away under pressure to allow delivery of the water to the cutting site in the same manner as conventional systems. The main advantage of the self-contained systems, unlike conventional systems is that the bottle can be depressurized, the water purged from the system and discarded, followed by the introduction of cleaning solutions into the bottle. The bottle is then pressurized again and these cleaning solutions distributed throughout the S-CDUWLIS to effectively decrease or eliminate biofilm contamination, thereby disinfecting the irrigation system pathway. Upon completion of this disinfection, the system can be purged of all cleaning solutions, rinsed, and fresh water reintroduced into the system for use. One method used and commercially available from a number of manufacturers is the addition of silver ions via nanoparticles to water. One associated drawback with these preparations is that taste is very unpleasant.

In light of the problems advanced above, there exists a need for a method of use of a dental cutting lubricant for providing physical cleansing of the cutting site, as well as improved cutting efficiency and bacteriostatic action necessary to provide decontamination maintenance of dental water lines.

SUMMARY OF THE INVENTION

In accordance with one form of the present invention, there is provided a method for dental cutting including the steps of: providing a dental unit water line irrigation system, the dental unit water line irrigation system including a container surrounding a solution chamber; providing a lubricant for use in the dental unit water line irrigation system, the lubricant defining a composition including 10 to 25% by weight of ethanol; 5 to 25% by weight of glycerol; 10 to 25% by weight of xylitol; 0.5 to 5% by weight of a nonionic surfactant and emulsifying agent; 0.15 to 0.5% by weight of a plurality of flavoring agents; and 45 to 60% by weight of water; and selectively operating the water line irrigation system to express the lubricant onto a dental cutting site.

In accordance with another form of the present invention, there is provided a method for dental cutting including the steps of: providing a dental unit water line irrigation system, the dental unit water line irrigation system including a container surrounding a solution chamber; providing a lubricant for use in the dental unit water line irrigation system, the lubricant defining a composition including 15 to 20% by weight of ethanol; 10 to 15% by weight of glycerol; 15 to 20% by weight of xylitol; 1 to 2% by weight of a nonionic surfactant and emulsifying agent; 0.15 to 0.25% by weight of spearmint oil; 0.05 to 0.1% by weight of peppermint oil; 0.04 to 0.08% by weight of 2-Methylbutyl acetate; 0.04 to 0.08% by weight of citric acid; 0.008 to 0.015% by weight of sodium percarbonate; 0.008 to 0.015% by weight of EDTA; 0.003 to 0.005% by weight of FD&C Blue No. 1 Lake; 0.0002 to 0.0004% by weight of silver nitrate; and 45 to 60% by weight of water; and selectively operating the water line irrigation system to express the lubricant onto a dental cutting site.

BRIEF DESCRIPTION OF THE DRAWINGS

For a fuller understanding of the nature of the present invention, reference should be made to the following detailed description, taken in conjunction with the accompanying drawings in which:

FIG. 1 is a perspective view, shown in partial cross section, of a dental unit water line irrigation system including a container surrounding a solution chamber for containing a lubricant.

Like reference numerals refer to like parts throughout the several views of the drawings.

DETAILED DESCRIPTION OF THE PREFERRED EMBODIMENTS

The formulation for use in dental unit waterlines for providing improved dental cutting efficiency and bacteriostatic action necessary to provide decontamination maintenance of dental water lines is described herein. Accordingly, one embodiment of the present invention is directed to a dental irrigation formulation including:

10 to 30% by weight of ethanol;
5 to 15% by weight of glycerol;
10 to 20% by weight of xylitol;
0.5 to 5% by weight of polysorbate 20;
0.15 to 0.5% by weight of flavoring agents;
51 to 77.5% by weight of water.

Ethanol may be present in a concentration of from 10 to 30% by weight, more preferably from 10 to 15% by weight based upon the total weight of the composition. Ethanol serves as a lubricant for increased cutting efficiency.

Glycerol may be present in a concentration of from 5 to 15% by the total weight of the composition and serves as a lubricant for increased cutting efficiency.

Xylitol may be present in a concentration of from 10 to 20% by the total weight of the composition and serves to reduce decay via exposure.

Polysorbate 20 (Sorbitan monolaurate) may be present in a concentration of from 0.5 to 5% by the total weight of the composition and serves as a nonionic surfactant and emulsifying agent.

The flavoring agents may be present in a concentration of from 0.15 to 0.5% by the total weight of the composition and serves as a flavor enhancing component. Non-limiting examples of flavoring agents include Spearmint [Mentha spicata] oil, Peppermint [Mentha piperita] oil, Wintergreen [Gaultheria procumbens] oil, and 2-Methylbutyl acetate.

Accordingly, the formulation may further include one or more of the following: citric acid (0.01 to 0.05%), sodium percarbonate (0.001 to 0.01%), FD&C Blue No. 1 Lake (0.001 to 0.01%), silver nitrate (0.0001 to 0.0010%), and tetrasodium ethylenediaminetetraacetic acid (EDTA). The citric acid serves as a mild buffering solution. The sodium percarbonate serves as an oxidizing agent. The FD&C Blue No. 1 Lake is a FDA-approved color additive which serves to provide a visual indicator of the irrigation supply level to dental personnel. The silver nitrate creates a bacteriostatic solution, which has been shown to inhibit recolonization of the small diameter water lines. The EDTA is a colorless, water-soluble solid that serves as a stabilizer.

The compositions of the present invention exhibit increased cutting efficiency and bacteriostatic action necessary to provide decontamination maintenance of dental water lines. The increased cutting efficiency promoted by the composition of the present invention results in less time and cost attributed per dental patient. The compositions of the present invention have high storage stability.

There is also provided a method for dental cutting including the steps of providing a dental unit water line irrigation system (10), the dental unit water line irrigation system (10) including a container surrounding a solution chamber (12); providing a lubricant (14) for use in the dental unit water line irrigation system (10), the lubricant (14) defining a composition including 10 to 25% by weight of ethanol; 5 to 25% by weight of glycerol; 10 to 25% by weight of xylitol; 0.5 to 5% by weight of a nonionic surfactant and emulsifying agent; 0.15 to 0.5% by weight of a plurality of flavoring agents; and 45 to 60% by weight of water; and selectively operating the water line irrigation system (10) to express the lubricant (14) onto a dental cutting site.

In accordance with another embodiment, there is provided a method for dental cutting including the steps of: providing a dental unit water line irrigation system (10), the dental unit water line irrigation system (10) including a container surrounding a solution chamber (12); providing a lubricant (14) for use in the dental unit water line irrigation system (10), the lubricant (14) defining a composition including 15 to 20% by weight of ethanol; 10 to 15% by weight of glycerol; 15 to 20% by weight of xylitol; 1 to 2% by weight of a nonionic surfactant and emulsifying agent; 0.15 to 0.25% by weight of spearmint oil; 0.05 to 0.1% by weight of peppermint oil; 0.04 to 0.08% by weight of 2-Methylbutyl acetate; 0.04 to 0.08% by weight of citric acid; 0.008 to 0.015% by weight of sodium percarbonate; 0.008 to 0.015% by weight of EDTA; 0.003 to 0.005% by weight of FD&C Blue No. 1 Lake; 0.0002 to 0.0004% by weight of silver nitrate; and 45 to 60% by weight of water; and selectively operating the water line irrigation system (10) to express the lubricant (14) onto a dental cutting site.

EXAMPLES

The compositions of the present invention are further illustrated by the examples below. The examples are only to illustrate the invention and should not be interpreted as limiting the scope of the invention since further modifications of the disclosed invention may be apparent to those skilled in the art. All such modifications are deemed to be within the scope of the claimed invention.

In a 750 mL solution of the dental irrigation formulation, one embodiment of the formulation includes:

| Ingredient | % W/W in 100 g | Purpose |
| --- | --- | --- |
| Ethanol | 16% | Lubricant |
| Glycerol | 10% | Lubricant |
| Xylitol | 13% | Decay prevention |
| Polysorbate 20 | 3% | Emulsifying agent |
| Spearmint oil | 0.15% | Taste |
| 2-Methylbutyl acetate | 0.05% | Taste |
| Silver nitrate | 0.000243% | Bacteriostatic |

Water 57.9% Solvent

In a 750 mL solution of the dental irrigation formulation, one embodiment of the formulation includes:

| Ingredient | % W/W in 100 g | Purpose |
| --- | --- | --- |
| Ethanol | 15% | Lubricant |
| Glycerol | 10% | Lubricant |
| Xylitol | 15% | Decay prevention |
| Polysorbate 20 | 5% | Emulsifying agent |
| Spearmint oil | 0.15% | Taste |
| 2-Methylbutyl acetate | 0.05% | Taste |
| Silver nitrate | 0.000243% | Bacteriostatic |
| Water | 54.8% | Solvent |

In a 750 mL solution of the dental irrigation formulation, one embodiment of the formulation includes:

| Ingredient | % W/W in 100 g | Purpose |
| --- | --- | --- |
| Ethanol | 15% | Lubricant |
| Glycerol | 10% | Lubricant |
| Xylitol | 15% | Decay prevention |
| Polysorbate 20 | 1% | Emulsifying agent |
| Spearmint oil | 0.186% | Taste |
| Peppermint oil | 0.06% | Taste |
| Wintergreen oil | 0.025% | Taste |
| 2-Methylbutyl acetate | 0.0477% | Taste |
| Citric acid | 0.032% | Buffering solution |
| Sodium percarbonate | 0.0081% | Oxidizing agent |
| EDTA | 0.0081% | Stabilizer |
| FD&C Blue No. 1 Lake | 0.004% | Visual identifier |
| Silver nitrate | 0.000243% | Bacteriostatic |
| Water | 58.63% | Solvent |

Results of the above-referenced example formulations have shown that dilute solutions of ethanol and glycerol added to dental irrigants can result in faster cutting rates of tooth structure with dental burs in high speed hand pieces. The mechanism of action is described as a chemo-mechanical effect. In the proposed formulation, ethanol and glycerol are used to increase cutting efficiency during tooth preparation. Additional agents are incorporated in the suggested formulation to act as emulsifiers. These can include polysorbate 80 and/or polysorbate 20. Emulsifiers offer the advantage of cleansing the work area by creating an emulsion of particulates and ground debris, as well as mucous and/or saliva that may be present in the oral cavity, making their removal from the field via evacuation easier.

In operation, the liquid formulation is intermittently introduced to the dental cutting site at a flow rate of approximately 30 ml/min for increasing the efficiency and safety of cutting a tooth structure (cooling), as well as the general experience for the patient with regards to taste and feel. Benefits of the dental irrigation formulation disclosed herein include:
(1) Disinfects and maintains water quality in small diameter dental unit water lines; (2) Provides pleasant taste and mouth feel for use in dental applications; (3) Improves cutting efficiency of tooth structure with diamond and carbide burs via chemo-mechanical effects; (4) Improves efficiency of ultrasonic cleaning tips used to clean teeth via chemo-mechanical defects; (5) Reduces bur clogging during preparation; (6) Helps dissolve and remove mucus and saliva during preparation, which results in cleaner final impressions; (7) May increase bond strength by removing smear layer during preparation; (8) Blue color helps dentist visualize the formulation fill levels in the bottle so that staff may be better prepared; and (9) May reduce cutting friction resulting in less hand piece maintenance.

Results have shown that increased cutting efficiency through use of the formulation of the present invention have decreased operation times by 60 minutes for certain procedures.

While the present invention has been shown and described in accordance with several preferred and practical embodiments, it is recognized that departures from the instant disclosure are contemplated within the spirit and scope of the present invention.

What is claimed is:

1. A method for dental cutting, said method comprising the steps of:
   providing a dental unit water line irrigation system, the dental unit water line irrigation system including a container surrounding a solution chamber;
   providing a lubricant for use in the dental unit water line irrigation system, the lubricant defining a composition comprising:
   (a) 10 to 25% by weight of ethanol;
   (b) 5 to 25% by weight of glycerol;
   (c) 10 to 25% by weight of xylitol;
   (d) 0.5 to 5% by weight of a nonionic surfactant and emulsifying agent;
   (e) 0.15 to 0.5% by weight of a plurality of flavoring agents; and
   (f) 45 to 60% by weight of water; and
   selectively operating the water line irrigation system to express the lubricant onto a dental cutting site.

2. The method for dental cutting as recited in claim 1 wherein the nonionic surfactant and emulsifying agent is selected from the group consisting of polysorbate 20, polysorbate 80, and mixtures thereof.

3. The method for dental cutting as recited in claim 1 wherein the plurality of flavoring agents is selected from a group consisting of spearmint oil, peppermint oil, wintergreen oil, 2-methylbutyl acetate, and mixtures thereof.

4. The method for dental cutting as recited in claim 1 wherein the plurality of flavoring agents comprises:
   (a) 0.15 to 0.25% by weight of spearmint oil;
   (b) 0.05 to 0.1% by weight of peppermint oil; and
   (c) 0.04 to 0.08% by weight of 2-Methylbutyl acetate.

5. The method for dental cutting as recited in claim 1 wherein said composition further comprises 0.04 to 0.08% by weight of citric acid.

6. The method for dental cutting as recited in claim 1 wherein said composition further comprises 0.008 to 0.015% by weight of sodium percarbonate.

7. The method for dental cutting as recited in claim 1 wherein said composition further comprises 0.003 to 0.005% by weight of a color additive.

8. The method for dental cutting as recited in claim 1 wherein said composition further comprises 0.008 to 0.015% by weight of EDTA.

9. A method for dental cutting, said method comprising the steps of:
   providing a dental unit water line irrigation system, the dental unit water line irrigation system including a container surrounding a solution chamber;
   providing a lubricant for use in the dental unit water line irrigation system, the lubricant defining a composition comprising:
   (a) 15 to 20% by weight of ethanol;
   (b) 10 to 15% by weight of glycerol;
   (c) 15 to 20% by weight of xylitol;
   (d) 1 to 2% by weight of a nonionic surfactant and emulsifying agent;
   (e) 0.15 to 0.25% by weight of spearmint oil;
   (f) 0.05 to 0.1% by weight of peppermint oil;
   (g) 0.04 to 0.08% by weight of 2-Methylbutyl acetate;
   (h) 0.04% to 0.08% by weight of citric acid;
   (i) 0.008 to 0.015% by weight of sodium percarbonate;

(j) 0.008 to 0.015% by weight of EDTA;
(k) 0.0002 to 0.0004% by weight of silver nitrate; and
(f) 45 to 60% by weight of water; and
selectively operating the water line irrigation system to express the lubricant onto a dental cutting site.

10. The method for dental cutting as recited in claim 9 wherein the nonionic surfactant and emulsifying agent is selected from the group consisting of polysorbate 20, polysorbate 80, and mixtures thereof.

11. The method for dental cutting as recited in claim 9 wherein said composition further comprises 0.003 to 0.005% by weight of a color additive.

12. The method for dental cutting as recited in claim 11 wherein said color additive is FD&C Blue No. 1.

* * * * *